US00PP08327P

United States Patent [19]

Schumann

[11] Patent Number: Plant 8,327

[45] Date of Patent: Jul. 27, 1993

[54] GERANIUM PLANT NAMED FISAM

[75] Inventor: Ingeborg Schumann, Münster, Fed. Rep. of Germany

[73] Assignee: Florfis AG, Binningen, Switzerland

[21] Appl. No.: 779,293

[22] Filed: Oct. 18, 1991

[51] Int. Cl.[5] ..... A01H 5/00
[52] U.S. Cl. ..... Plt./87.12
[58] Field of Search ..... Plt./87.12

*Primary Examiner*—James R. Feyrer
*Attorney, Agent, or Firm*—Foley & Lardner

[57] ABSTRACT

A new and distinct cultivar of geranium named Fisam, particularly characterized by the combined features of large, light violet flowers, double flower form, very early flower response, medium green foliage with strong zonation, medium growth characteristics, and fast rooting ability.

1 Drawing Sheet

The present invention comprises a new and distinct cultivar of geranium, botanically known as *Pelargonium peltatum* L'Hert, and hereinafter referred to by the cultivar name Fisam.

Fisam is a product of planned breeding program which had the objective of creating new geranium cultivars with violet flower color, good cultivation ability, and possibly with other unique characteristics in order to provide a possible replacement for the well known commercial cultivar Amethyst.

Fisam was originated from a hybridization made by the inventor Ingeborg Schumann in a controlled breeding program in Galdar, Gran Canaria, Spain in 1985. The female parent was an unnamed hybrid, originated from crossing a hybrid resulting from a cross of Salmon Queen and Amethyst, with an inbred line of Rouletta. The male parent of Fisam was Bardo Lolli, characterized by large, dark rose semi-double flowers.

Fisam was discovered and selected as one flowering plant within the progeny of the stated cross by Ingeborg Schumann in spring 1986 in a controlled environment in Galdar, Gran Canaria, Spain.

The first act of asexual reproduction of Fisam was accomplished when vegetative cuttings were taken from the initial selection in February 1987 in a controlled environment in Hillschend, Federal Republic of Germany by, or under the supervision of, Ingeborg Schumann.

Horticultural examination of rooted cuttings initiated in May 1987 and continuing thereafter has demonstrated that the combination of characteristics as herein disclosed for Fisam are firmly fixed and are retained through successive generations of asexual reproduction.

Fisam has not been observed under all possible environmental conditions. The phenotype may vary somewhat with variations in environment such as temperature, light intensity and day length, without, however, any variance in the genotype. The following observations measurements, and comparisons describe plants grown in Hillscheid, Federal Republic of Germany under greenhouse conditions which approximate those generally used in commercial practice.

The following traits have been repeatedly observed and are determined to be basic characteristics of Fisam, which in combination distinguish this geranium as a new and distinct cultivar:

1. Large double flowers of light violet color, with purple markings on upper petals
2. Very early flower response
3. Rich flower production
4. Medium green foliage with strong zonation
5. Medium to strong growth
6. Good and fast rooting ability
7. Good branching characteristics Of the many commercial cultivars known to the present inventor, the most similar in comparison to Fisam is Amethyst. Reference is made to attached Chart A which compares certain characteristics of Fisam to those same characteristics of Amethyst. In general comparison to Amethyst, Fisam has a lighter violet flower color, more regular shape of umbels, more vigorous growth, a much earlier flower response, and better rooting characteristics of the cuttings.

The accompanying color photographic drawing is a side elevational view showing typical flower and foliage characteristics of Fisam, with colors being as true as possible with illustrations of this type.

In the following description color references are made to The Royal Horticultural Society Colour Chart. The color values were determined indoors from flowers taken from plants grown outdoors in June at Hillscheid, Federal Republic of Germany.

Classification:

*Botanical.*—A hybrid of the species *Pelargonium peltatum* L'Hert.

*Commercial.*—Ivy geranium, cv. Fisam.

INFLORESCENCE

A. Umbel:

*Average diameter.*—100 mm.
*Average depth.*—59 mm.
*Peduncle length.*—130 mm.
*Pedicel length.*—25 mm.
*Pedicel color.*—Light green.
*Number of flowers per umbel.*—7.7.

B. Corolla:

*Average diameter.*—55 mm.
*Form.*—Double.
*Number of petals.*—11-14.
*Color (general tonality from a distance of three meters).*—Light violet.

*Color of upper side of petals.*—R.H.S. 77C with purple markings in the form of two parallel veins and a small dot in the middle appearing on the upper petals; inner petals near upper petals may show weak marking of same type.

*Color of lower side.*—R.H.S. 77C.

*Number of sepals.*—5.

*Color of sepals.*—Light green, no anthocyanin.

*Petaloids.*—There is an average of two or three small petals with a stamen on top; petaloids are essentially transformed anthers.

C. Bud:

*Shape.*—Elongated.

*Color (sepals).*—Green.

*Color (tips of petals).*—Light violet.

D. Reproductive organs:

*Androecium.*—5–8 anthers, 4–6 fertile with orange pollen.

*Gynoecium.*—5–6 lobed stigma, purple.

E. Spring flowering response period: In Hillscheid, Federal Republic of Germany in 1989, 95% of plants with at least 1 flower opened 11 weeks after planting of unrooted cuttings.

F. Outdoor flower production: The flower count in 1989 in Hillscheid, Federal Republic of Germany indicated between 160 and 165 flowers per plant for May through September observation period.

G. Durability: No shattering.

H. Seed production: Fisam is fertile and produces seed after pollination, but sets only a few seeds spontaneously.

PLANT

A. Foliage:

*Form.*—Ivy shaped.

*Margin.*—Entire.

*Color (upper surface).*—Medium green, approximately R.H.S. 137C.

*Color (zonation).*—Brown, forming a narrow ring, R.H.S. 166A.

*Tolerance of botyrytis.*—Good.

B. General appearance and form:

*Internode length.*—2.5–3 cm.

*Branching pattern.*—6.3 after 12 weeks of growing time.

*Height.*—65 cm in August.

CHART A

| | FISAM | AMETHYST |
|---|---|---|
| Flower color | Light violet 77C | violet 78B |
| Diameter of flower | 5.6 cm | 5.1 cm |
| Growth habit | medium | weak-medium |
| Beginning of flowering (percent flowering plants in 11th week) | 95% | 0% |
| Rooting of cuttings | good/fast | bad/slow |

I claim:

1. A new and distinct cultivar of geranium plant named Fisam, as illustrated and described.

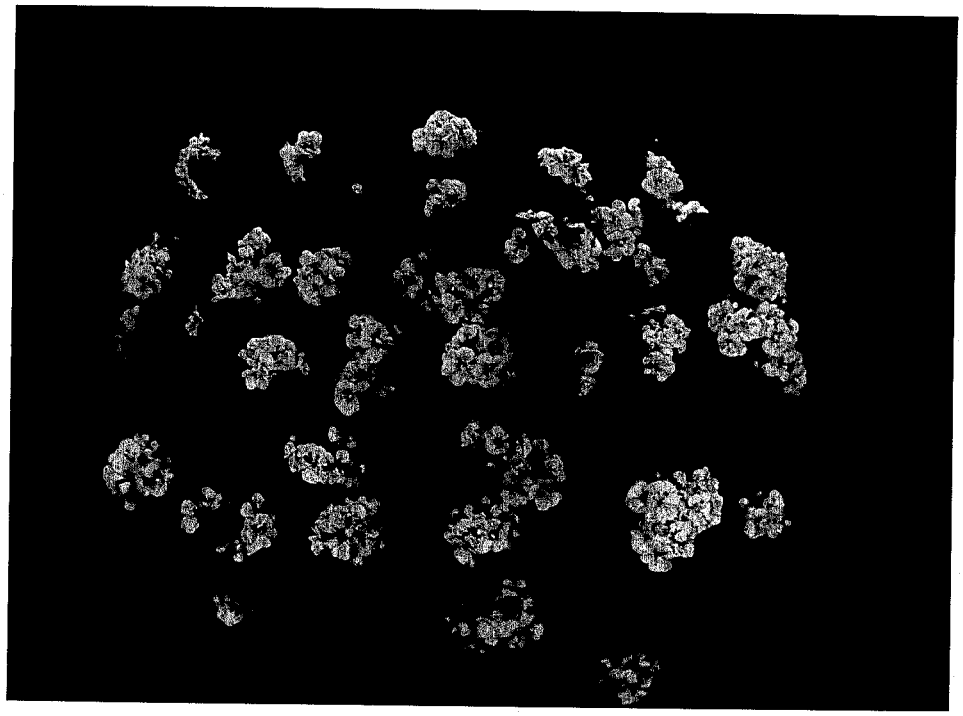

* * * * *